US012575379B2

(12) United States Patent
Kouzminov et al.

(10) Patent No.: US 12,575,379 B2
(45) Date of Patent: Mar. 10, 2026

(54) MEASUREMENT OF LATERAL DOPANT CONCENTRATION AND DISTRIBUTION IN HIGH ASPECT RATIO TRENCH STRUCTURES

(71) Applicant: Applied Materials, Inc., Santa Clara, CA (US)

(72) Inventors: Dimitry Kouzminov, Beverly, MA (US); Vikram M. Bhosle, North Reading, MA (US); Arun Ramaswamy Srivatsa, Fremont, CA (US); Ming Hong Yang, Campbell, CA (US)

(73) Assignee: Applied Materials, Inc., Santa Clara, CA (US)

( * ) Notice: Subject to any disclaimer, the term of this patent is extended or adjusted under 35 U.S.C. 154(b) by 366 days.

(21) Appl. No.: 18/212,136

(22) Filed: Jun. 20, 2023

(65) Prior Publication Data

US 2024/0429105 A1 Dec. 26, 2024

(51) Int. Cl.
*H01L 21/66* (2006.01)
*G01N 23/2258* (2018.01)
*G01N 33/00* (2006.01)

(52) U.S. Cl.
CPC ......... *H01L 22/12* (2013.01); *G01N 23/2258* (2013.01); *G01N 33/00* (2013.01); *G01N 33/0095* (2024.05)

(58) Field of Classification Search
None
See application file for complete search history.

(56) References Cited

U.S. PATENT DOCUMENTS 9,786,495 B2    10/2017    Shimomura
2024/0429105 A1*    12/2024    Kouzminov ........... H01L 22/20

* cited by examiner

*Primary Examiner* — Jack S Chen
(74) *Attorney, Agent, or Firm* — KDW Firm PLLC

(57) ABSTRACT

Disclosed herein are approaches for measuring lateral dopant concentration and distribution in high aspect radio trench structures. In one approach, a method may include providing a substrate including a plurality of alternating vertical structures and trenches, and removing a portion of the substrate to expose a sidewall of the first vertical structure of the plurality of structures. The method may further include directing a spectrometry beam into the sidewall of the first vertical structure to determine a dopant characteristic of the first vertical structure, wherein the spectrometry beam is delivered perpendicular to a plane defined by the sidewall of the first vertical structure.

15 Claims, 7 Drawing Sheets

300

MEASUREMENT OF LATERAL DOPANT CONCENTRATION AND DISTRIBUTION IN HIGH ASPECT RATIO TRENCH STRUCTURES

FIELD OF THE DISCLOSURE

The present disclosure relates to semiconductor structure implant diagnostics and, more particularly, to approaches for measuring lateral dopant concentration and distribution in high aspect radio trench structures.

BACKGROUND OF THE DISCLOSURE

Decreasing the dimensions of electronic devices and increasing the level of their integration are two major trends in current electronic device manufacturing. As a result of these trends, the density of elements forming a semiconductor device continuously increases. The shrinkage of the semiconductor devices involves performing the routine fabrication of the semiconductor device elements but on the submicron level.

Typically, an electronic device is fabricated on a wafer using many layers of films. Generally, layers of various semiconducting, conducting and insulating materials are used to form the integrated circuits. These layers may be doped, deposited and etched to form electronic devices.

As devices shrink, and aspect ratios of device structures increases, controlled doping becomes more challenging. Therefore, it is desirable to determine dopant levels in various device structures, particularly those with high aspect ratios. One current approach includes Adam Probe Tomography (APT). However, APT suffers from high detection limits, low mass resolution, high expense, and high processing times. Secondary ion mass spectrometry (SIMS) is another approach used for dose detection. However, dopant measurements relative to the dimensions of current 3-D structures is limited. Therefore, there is a need in the art for improved techniques to detect dose characteristics in semiconductor structures with high aspect ratios.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In one aspect, a method may include providing a substrate including a plurality of alternating structures and trenches, removing a portion of the substrate to expose a sidewall of a first structure of the plurality of structures, and directing a spectrometry beam into the sidewall of the first structure to determine a dopant characteristic of the first structure, wherein the spectrometry beam is delivered perpendicular to a plane defined by the sidewall of the first structure.

In another aspect, a method for determining dopant characteristics of a plurality of vertical structures may include providing a doped layer over the plurality of vertical structures of a substrate, and removing a portion of the substrate to expose a sidewall of a first vertical structure of the plurality of structures. The method may further include directing a spectrometry beam into the sidewall of the first vertical structure to determine a dopant distribution profile and a dopant concentration of the first vertical structure, wherein the spectrometry beam is delivered perpendicular to a plane defined by the sidewall of the first vertical structure.

In yet another aspect, a system may include a processor and a memory storing instructions executable by the processor to form a doped layer over a plurality of alternating vertical structures and trenches of a substrate, wherein following the formation of the doped layer, a portion of the substrate is removed to expose a sidewall of a first vertical structure of the plurality of alternating vertical structures and trenches, and a spectrometry beam is directed into the sidewall of the first vertical structure to determine a dopant distribution profile and a dopant concentration of the first vertical structure, and wherein the spectrometry beam is delivered perpendicular to a plane defined by the sidewall of the first vertical structure.

BRIEF DESCRIPTION OF THE DRAWINGS

The accompanying drawings illustrate exemplary approaches of the disclosure, including the practical application of the principles thereof, as follows.

Figures 1, 2:
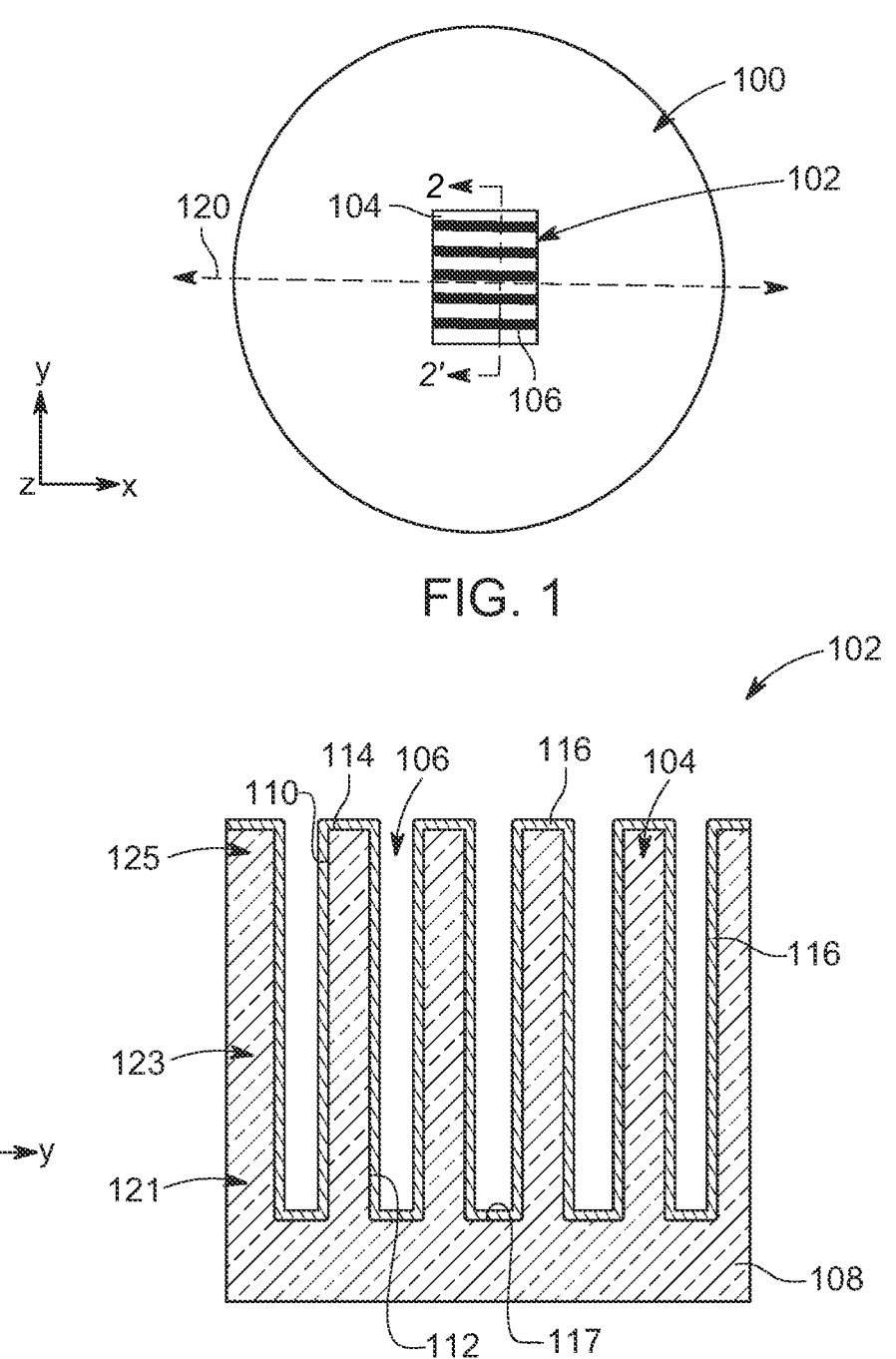
FIG. 1 illustrates a top view of a device, including a plurality of alternating vertical structures and trenches in a substrate, according to embodiments of the present disclosure.
FIG. 2 illustrates a side cross-sectional view of the plurality of alternating vertical structures and trenches in the substrate, according to embodiments of the present disclosure.

The drawings are not necessarily to scale. The drawings are merely representations, not intended to portray specific parameters of the disclosure. The drawings are intended to depict exemplary embodiments of the disclosure, and therefore are not to be considered as limiting in scope. In the drawings, like numbering represents like elements.

Furthermore, certain elements in some of the figures may be omitted, or illustrated not-to-scale, for illustrative clarity. The cross-sectional views may be in the form of "slices", or "near-sighted" cross-sectional views, omitting certain background lines otherwise visible in a "true" cross-sectional view, for illustrative clarity. Furthermore, for clarity, some reference numbers may be omitted in certain drawings.

DETAILED DESCRIPTION

Devices, semiconductor structures, and methods in accordance with the present disclosure will now be described more fully hereinafter with reference to the accompanying drawings, where various embodiments are shown. The devices, semiconductor structures, and methods may be embodied in many different forms and are not to be construed as being limited to the embodiments set forth herein. Instead, these embodiments are provided so the disclosure will be thorough and complete, and will fully convey the scope of the methods to those skilled in the art.

As mentioned above, many key applications (e.g., CMOS Image Sensor, NAND, 3D DRAM, Logic) use sidewall doping, typically for high aspect ratio (HAR) trenches. Challenges exist, however, when it comes to determining and managing dopants. For example, characterization of lateral dopant distribution (e.g., concentration and profile) and chemical composition in deep trench structures for a range of composition (from trace levels ~E16-E17 cm-3 to stoichiometric analysis) is difficult to achieve. No viable secondary ion mass spectrometry (SIMS) based solution exists, which is needed for low detection limit. Although atom probe tomography solutions exist, these solutions suffer from poor detection limit (e.g., E18-E19 cm-3), poor mass resolution, high expense, low throughput, and low yield.

Embodiments of the present disclosure address these deficiencies by providing a lateral SIMS trench sidewall profiling technique, which provides for quantitative measurement of dopant concentration in the trench sidewall as a function of proximity to a trench using a ultra-shallow junction (USJ) profiling technique. As will be described herein, the sidewall dopant distribution is measured through the wafer cross-section, as opposed to only top-down, which is the conventional approach. In some embodiments, the wafer is cleaved using a precision micro-cleaver (PMC) along a trench line, and the cleaved wafer is then flipped 90 degrees so the wafer cross-section faces an SIMS ion beam. The sample may be mounted in a specially designed fixture, which in its turn loaded into SIMS tool sample holder. A low energy (e.g., 300 eV) SIMS primary beam is used to produce the dopant distribution profile for the trench sidewall(s).

In some embodiments, determining the dopant concentration may involve a two-step data collection methodology, wherein a first measurement includes a 1.5D SIMS for dopant dose in the sidewall, and a second measurement includes a lateral SIMS for dopant distribution in the sidewall. The 1.5-D SIMS can be used to study dopant incorporation in 3-D structures, such as the trench sidewall, while the second measurement can be used for greater visibility into the doping. More specifically, this methodology for data analysis and quantification of results is used to derive lateral composition, wherein the quantitative analysis of dopant distribution in the sidewall is done by depth calibration (e.g., using internal depth calibration standard or x-section data for fin spacing) first, and then concentration calibration using dopant sidewall dose. Conventional SIMS approaches are based on comparing dopant-to-matrix (Si) signal ratios for the standard and the sample with both signals originating from the same area on the sample. While this stands for the standard, it doesn't for the sample since Si comes from the entire imaged area (e.g., ~30 µm square) and the dopant signal comes only from the small part of it, such as the sidewall. Thus, two measurements are required for optimal results.

In some embodiments, sidewall dopant concentration quantification is done as follows. A SIMS erosion rate is measured either using internal depth calibration standard (e.g., sequence of Si/5% Ge deltas in Si with 4.2 nm spacing) or by using TEM from trench x-section, and lateral depth calibrated. Dopant concentration calibration may be done by applying dopant dose measured in 1.5D SIMS to the count vs. depth plot using a formula which will be described in greater detail below. The new approaches described herein are highly valuable for plasma doping (PLAD) applications, for example.

FIG. 1 illustrates a top view of a wafer or substrate 100. The substrate 100 may include a plurality of processing areas 102, wherein the example processing area 102 includes a plurality of alternating vertical structures (e.g., fins) 104 and trenches 106. Although enlarged for ease of viewing, it will be appreciated that the substrate 100 may include thousands or millions of processing areas 102. The plurality of alternating vertical structures 104 and trenches 106 may be formed from the substrate 102 using any combination of subtractive (e.g., etch) and/or additive (e.g., deposition) processes, as is known, and the plurality of alternating vertical structures 104 and trenches 106 may be the same or a different material as the substrate 100.

FIG. 2 demonstrates a side cross-sectional view of the plurality of alternating vertical structures 104 and trenches 106 of the processing area 102 in greater detail. As shown, the vertical structures (hereinafter "structures") 104 may extend from a base 108, and may each include a first sidewall 110, a second sidewall 112 opposite the first sidewall 110, and a top surface 114 connecting the first sidewall 110 and the second sidewall 112. The structures 104 may extend parallel to one another, and may define the trenches 106. A bottom surface 117 of each trench 106 may extend between adjacent structures 104. Each of the structures 104 may include a first (e.g., bottom) portion 121, a second (e.g., middle) portion 123, and a third (e.g., upper) portion 125, as shown.

As further shown, a doped layer 116 may be formed over each of the structures 104, including within each of the trenches 106. More specifically, the doped layer 116 may be conformally formed along the first sidewall 110, the second sidewall 112, the top surface 114, and the bottom surface 117. In some embodiments, the doped layer 116 may be formed by depositing a dopant material along all exposed surfaces of the processing area 102 using, e.g., a plasma immersion or plasma doping (PLAD) process. In some embodiments, the substrate 100 and the doped layer 116 may be subjected to one or more annealing processes to further cause penetration of the dopant into the structures 104. Other doping techniques are possible within the scope of the present disclosure.

Referring again to FIG. 1, the substrate 100 may then be cut or cleaved along a cleave line 120. In some embodiments, the substrate 100 is cleaved using a precision microcleaver (PMC), wherein the substrate 100 is cleaved precisely along the trench to provide a good quality sample in which a single sidewall is present within the imaged field, excellent depth resolution is achieved, and no "ghost" profiles are generated. Although the cleave line 120 generally dissects the substrate 100 into two equal halves, this is done for ease of explanation and is not dispositive.

Figure 3:
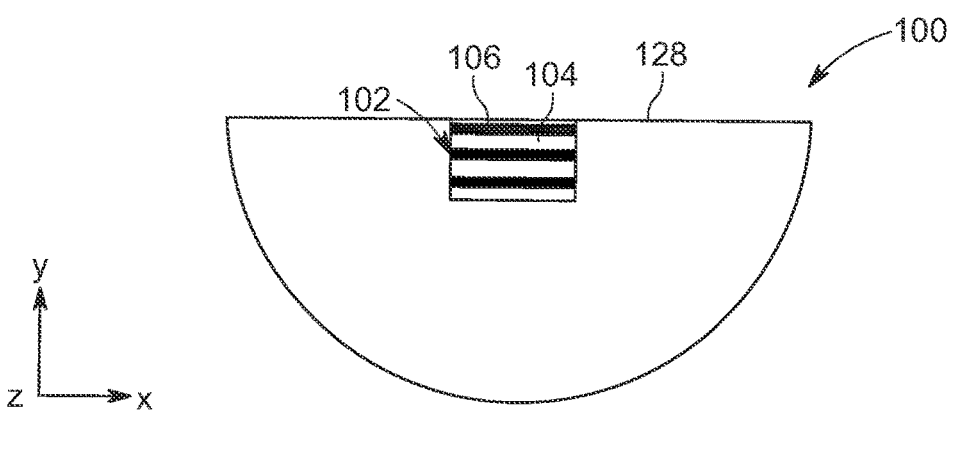
FIG. 3 illustrates a top view of the device following a cleaving operation on the substrate, according to embodiments of the present disclosure.

FIG. 3 demonstrate the substrate 100 following the cleaving process. As shown, the cut exposes a sidewall surface 128 of one of the structures 104. In some embodiments, the sidewall surface 128 may correspond to the first sidewall 110. In other embodiments, the cleaving process removes the first sidewall 110 such that the sidewall surface 128 is further towards a center of cleaved structure 104.

Figure 4:
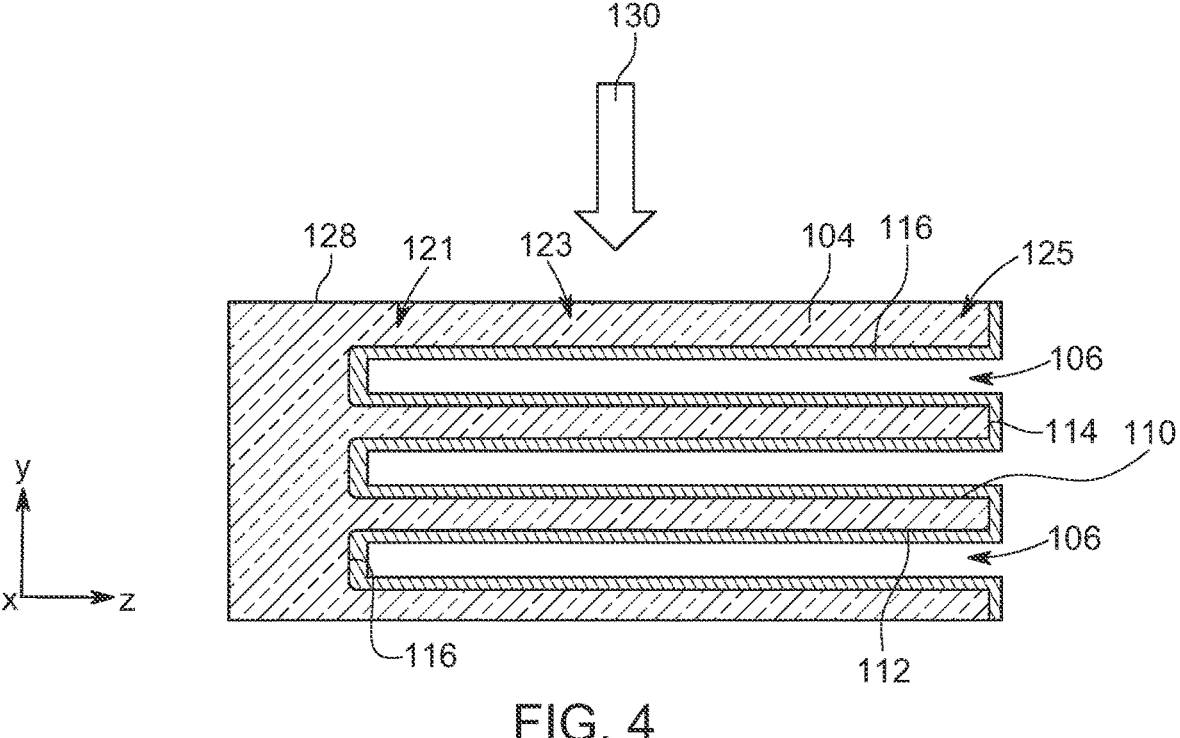
FIG. 4 illustrates a side view of the substrate during a spectrometry process to determine dopant characteristics of the plurality of alternating vertical structures and trenches in the substrate, according to embodiments of the present disclosure.

FIG. 4 demonstrates the processing area 102 following the cleaving process and following rotation of the substrate 100. In the orientation shown, the sidewall surface 128 is facing up (e.g., along the y-direction), and the top surface 114 of each structure 104 is facing to the side (e.g., along the z-direction). With the substrate 100 in this orientation, a low energy (e.g., 300 eV) SIMS beam 130 may be directed to the sidewall surface 128 to produce a dopant distribution profile. More specifically, the SIMS beam 130 is used to profile a lateral composition variation as a function of trench/structure depth via lateral profiling at different sections of the structure with a distance or step size of 25 μm, for example. Said differently, the SIMS beam 130 may scan and collect measurements along an entire length of the sidewall surface 128 to generate the composition profile for the structure 104.

Figures 5A, 5B:
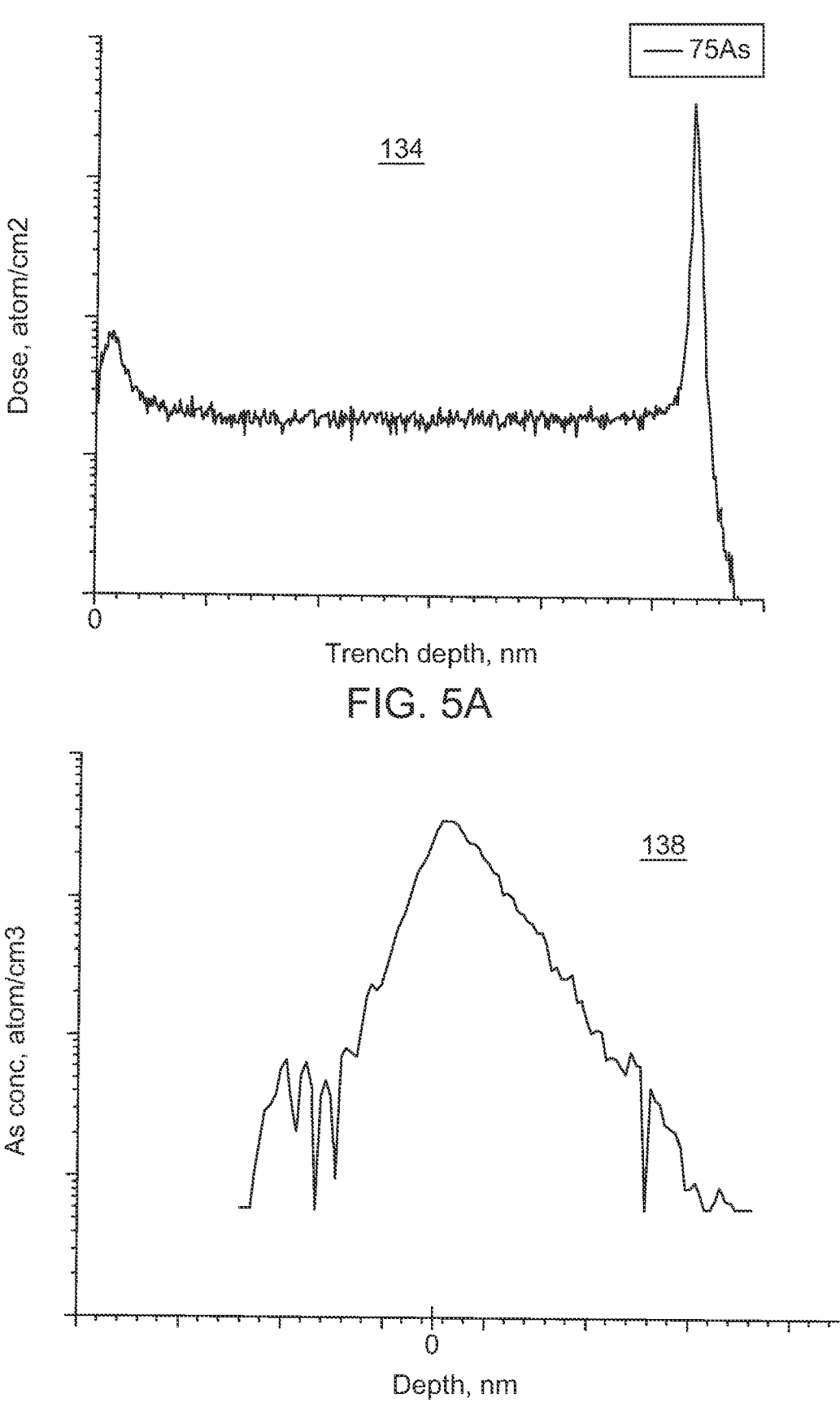
FIG. 5A is a graph illustrating dopant dose vs. trench depth distribution, according to embodiments of the present disclosure.
FIG. 5B is a graph illustrating an example dopant concentration calibration, according to embodiments of the present disclosure.

In some embodiments, prior to scanning the SIMS beam 130 along the sidewall surface 128, a first measurement process may be performed whereby a 1.5D SIMS is performed top-down on the processing area 102, e.g., at 1 keV 02+, resulting in the dopant dose vs. trench depth distribution demonstrated by graph 134 in FIG. 5A. As known, 1.5 SIMS is a pseudo 2-D method for conformal doping measurements.

Following the first measurement process, the substrate 100 may cleaved and mounted in a fixture for performance of the second measurement, i.e., the lateral SIMS measurement of the sidewall surface 128, which may be performed at 300 eV O2+. A depth calibration may be performed using an internal depth calibration standard (e.g., series of Si/5% Ge delta structures in Si) or TEM x-section, and a dopant concentration calibration C(x) may be performed according to the following equation:

$$C(x)=I(x)*D/(\int I(x)*dx),$$

wherein C(x) is dopant concentration (at/cm3) at depth x, I(x) is the dopant SIMS count rate at depth x, and D is the mean dopant dose in the sidewall (at/cm2). Graph 138 of FIG. 5B demonstrates an example dopant concentration calibration C(x) according to this equation.

In some non-limiting embodiments, sidewall dopant concentration quantification may be done as follows. A SIMS erosion rate may be measured either using internal depth calibration standard (e.g., sequence of Si/5% Ge deltas in Si with 4.2 nm spacing) or by using TEM from trench x-section, and then the lateral depth calibrated. The dopant concentration calibration may be done by applying dopant dose measured in 1.5D SIMS to the count vs. depth plot through the above formula C(x).

Figure 6A:
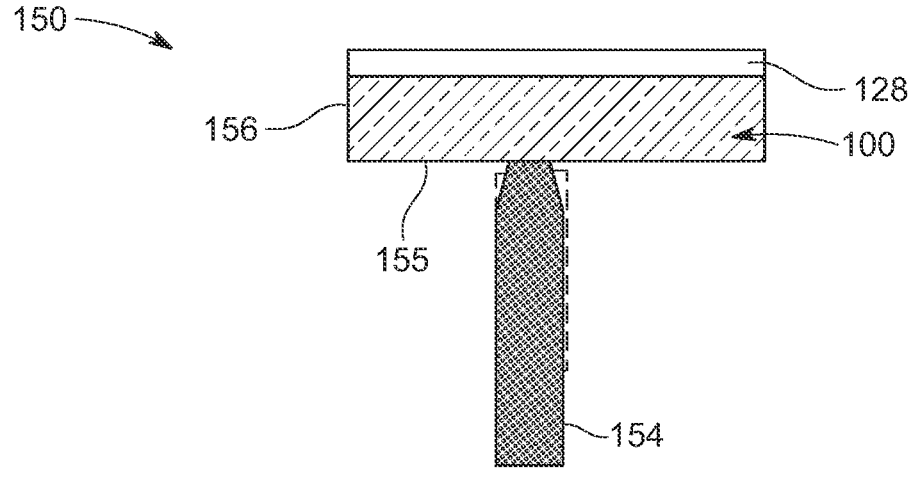
FIG. 6A is a top view of a fixture for holding the substrate, according to embodiments of the present disclosure.
Figure 6B:
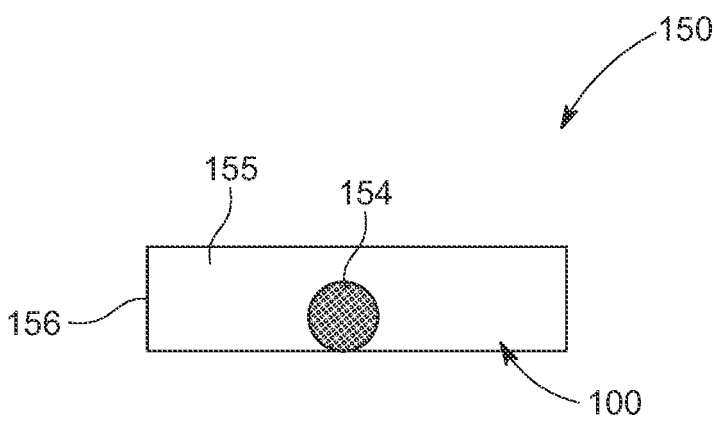
FIG. 6B is a side view of the fixture for holding the substrate, according to embodiments of the present disclosure.

The top view of FIG. 6A and the side view of FIG. 6B demonstrate an example fixture 150 capable of housing the substrate 100 after it's been cleaved. Because the shape of the substrate 100 changes as a result of the cleaving operation, the fixture 150 is necessary to prevent physical contact with the sidewall surface 128, and to orient the sidewall surface 128 towards the SIMS beam for processing. In the embodiment shown, a screw 154 may be secured to an underside 155 of the substrate 100, and only an exterior edge 156 of the substrate 100 may be in contact with the fixture 150. After the substrate 100 is mounted within the fixture 150, the fixture 150 can then be loaded into a SIMS tool sample holder (not shown). It will be appreciated that alternative designs for the fixture 150 are capable in other embodiments.

Figure 7:
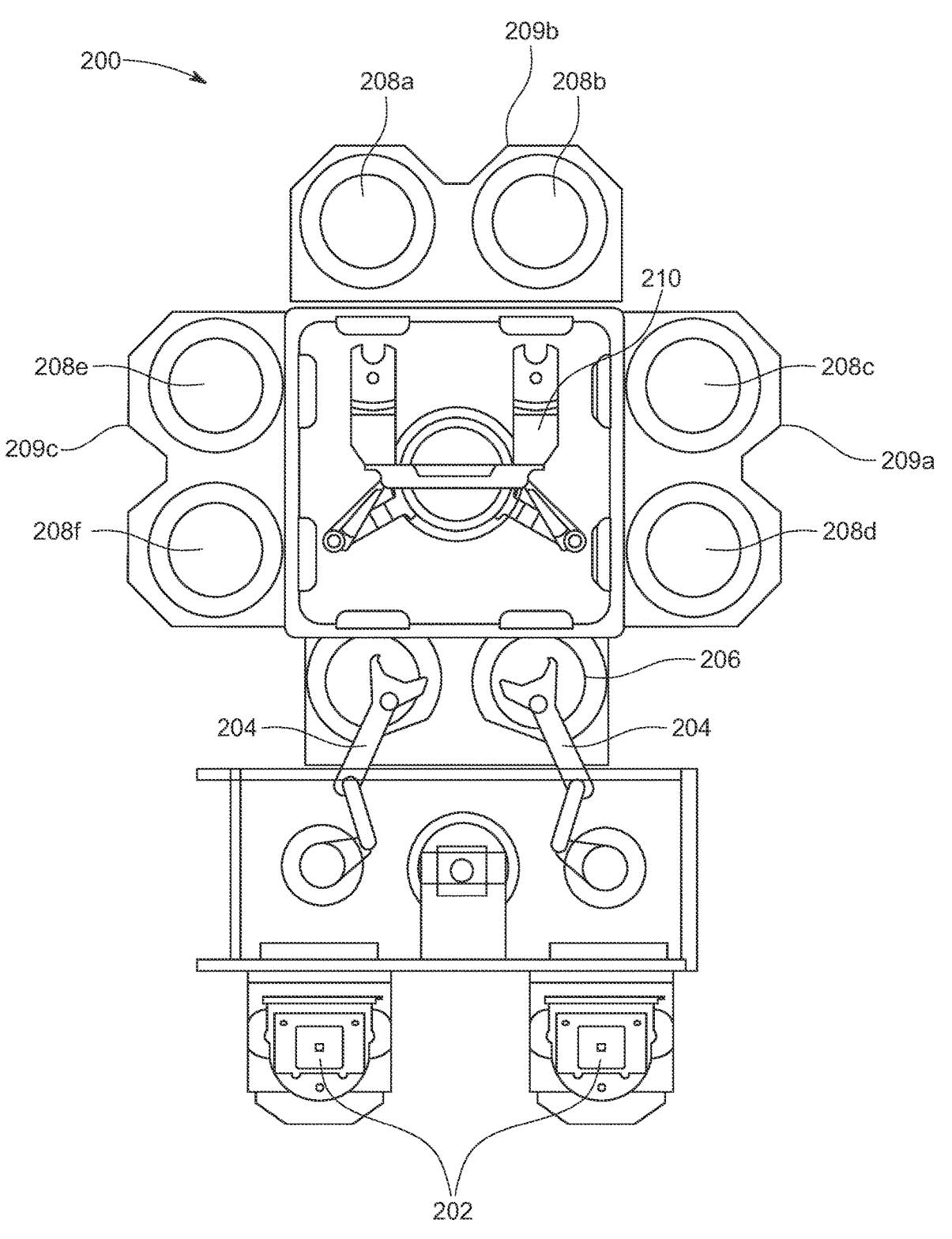
FIG. 7 is a processing system, according to embodiments of the present disclosure.

FIG. 7 illustrates a top plan view of one embodiment of a processing system 200 including deposition, etching, baking, and curing chambers according to some embodiments. The processing system 200 may be used to perform the operations described herein. As shown, a pair of front opening unified pods 202 supply substrates of a variety of sizes that are received by robotic arms 204 and placed into a low pressure holding area 206 before being placed into one of the substrate processing chambers 208a-f, positioned in tandem sections 209a-c. A second robotic arm 210 may be used to transport the substrate wafers from the holding area 206 to the substrate processing chambers 208a-f and back. Each substrate processing chamber 208a-f, can be outfitted to perform a number of substrate processing operations including dopant implants, wafer cleaving, and SIMS measurement processes, as described above.

The processing chambers 208a-f are further capable of layer deposition, etching, pre-cleaning, annealing, plasma processing, degas, orientation, and other substrate processes. Any number of other processing systems may be utilized with the present technology, which may incorporate chambers for performing any of the specific operations. In some embodiments, chamber systems which may provide access to multiple processing chambers while maintaining a vacuum environment in various sections, such as the noted holding and transfer areas, may allow operations to be performed in multiple chambers while maintaining a particular vacuum environment between discrete processes.

The processing system 200, or more specifically, chambers incorporated into the processing system 200 or other processing systems, may be used to produce structures according to some embodiments of the present disclosure. For example, the processing system 200 may be used to form a doped layer over a plurality of alternating vertical structures and trenches of a substrate, wherein following the formation of the doped layer, a portion of the substrate is removed to expose a sidewall of a first vertical structure of the plurality of alternating vertical structures and trenches, and a spectrometry beam is directed into the sidewall of the first vertical structure to determine a dopant distribution profile and a dopant concentration of the first vertical structure, and wherein the spectrometry beam is delivered perpendicular to a plane defined by the sidewall of the first vertical structure.

A system controller (not shown) is in communication with the various components of the system 200, including the robots and the processing chambers 208a-f. The system controller can be a computer including a central processing unit, memory, suitable circuits/logic/instructions, and storage.

Processes or instructions may generally be stored in the memory of the system controller as a software routine that, when executed by the processor, causes the processing chambers 208a-f to perform processes of the present disclosure. The software routine may also be stored and/or executed by a second processor (not shown) that is remotely located from the hardware being controlled by the processor. Some or all of the method(s) of the present disclosure may also be performed in hardware. As such, the process may be implemented in software and executed using a computer system, in hardware as, e.g., an application specific integrated circuit or other type of hardware implementation, or as a combination of software and hardware. The software routine, when executed by the processor, transforms the general purpose computer into a specific purpose computer (controller) that controls the chamber operation such that the processes are performed.

Figure 8:
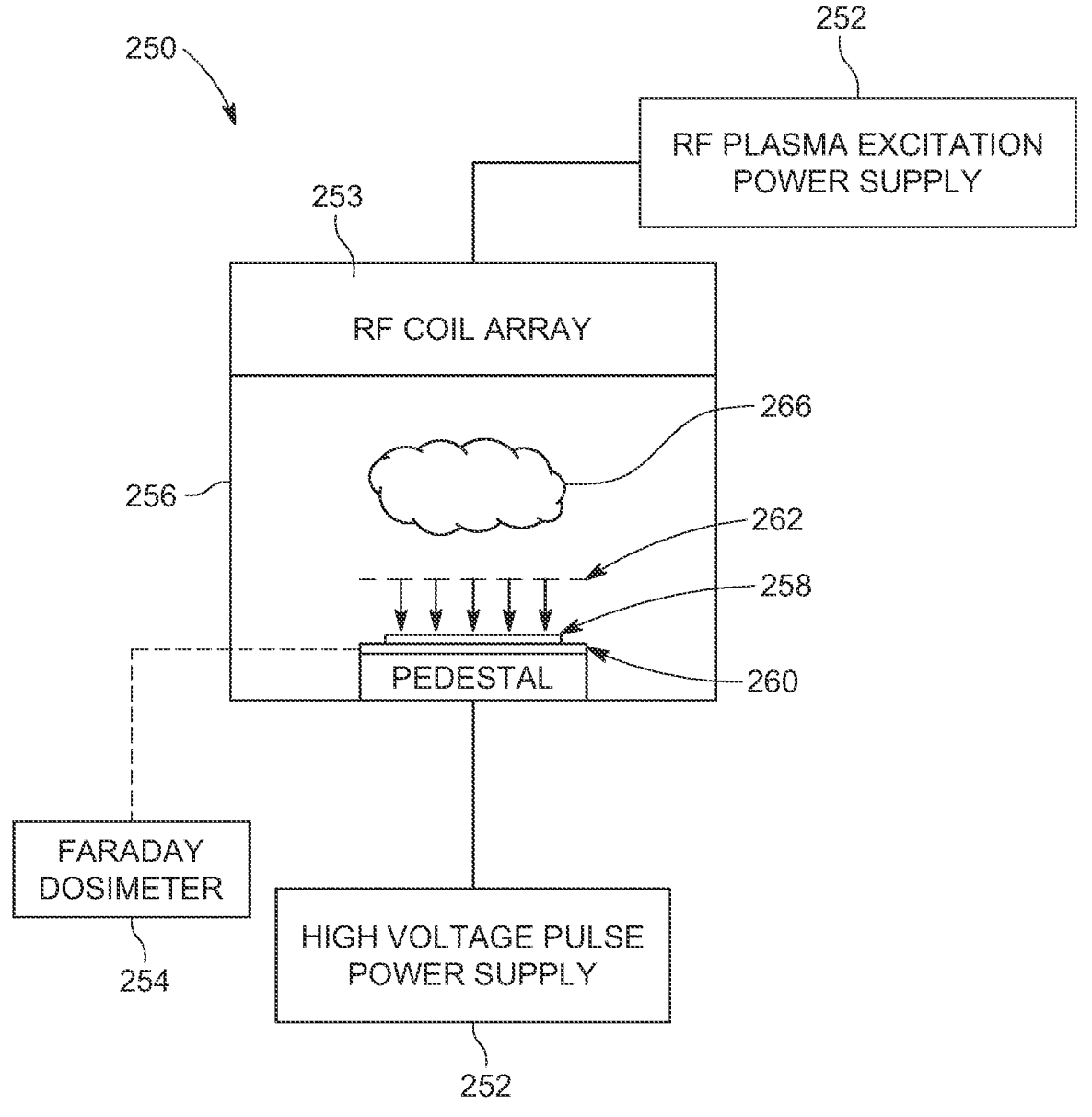
FIG. 8 is a plasma doping system, according to embodiments of the present disclosure.

In some embodiments, one of the processing chambers 208a-f may include a plasma immersion or PLAD tool operable to form the doped layer 116, as described above. FIG. 8 demonstrates an example, non-limiting PLAD tool or system, which provides pulsed RF-excited continuous plasma doping. As shown, the system 250 may include a plasma power supply 251, a voltage pulse power supply 252, an RF coil array 253, and a dosimeter 254. Within a plasma chamber 256 is a wafer/substrate 258, which may be the same or similar to the substrate 100 described above. A platen/pedestal 260 may support the wafer 258, and a sheath 262 may be formed above the wafer 258. The dosimeter 254 may be a Faraday dosimeter or other type of sensor that directly measures the dose of ions received by the wafer 258. Although non-limiting, the dosimeter can be located on the pedestal 260, proximate to the wafer 258.

During use, the plasma power supply 252 and the RF coil array 253 deliver radio frequency excitation to generate a plasma 266 when gaseous species are delivered into the plasma chamber 256. For example, the plasma power supply 251 may be an RF powered inductively coupled power source to generate inductively coupled plasma 266, as known in the art. Gaseous species may be delivered from one or more gas sources (not separately shown) to generate ions of any suitable species, such as fluorine.

The voltage pulse power supply 252 may generate a bias voltage between the wafer 258 and the plasma chamber 256. As such, when the voltage pulse power supply 252 generates a voltage between the plasma chamber 256 and the substrate 258, a similar, but slightly larger, voltage difference is generated between the plasma 266 and the substrate 258. In one non-limiting example, a 5000 (5 kV) voltage difference established between the plasma chamber 256 and the substrate 258 (or, equivalently, pedestal 214) may generate a voltage difference of approximately 5005 V to 5030 V between the plasma 266 and the substrate 258.

In some embodiments, the voltage pulse power supply 252 may generate a bias voltage as a pulsed voltage signal, wherein the pulsed voltage signal is applied in a repetitive and regular manner, to generate a pulse routine comprising a plurality of extraction voltage pulses. For example, a pulse routine may apply voltage pulses of 500 V magnitude, 1000 V magnitude, 2000 V magnitude, 5000 V magnitude, or 10,000 V magnitude in various non-limiting embodiments. The system 250 may further include a controller (not shown), to control the pulsing routine applied to the substrate 258.

According to various embodiments, the plasma 266 may be formed at least in part of ions that constitute an amorphizing species, wherein the amorphizing species may be any suitable ion capable of amorphizing an initially crystalline region of materials, such as the substrate 258. When the plasma 266 is present in the plasma chamber 256, the controller may generate a signal for the voltage pulse power supply 252 to apply a pulse routine to the substrate 258, where the pulse routine constitutes a plurality of extraction voltage pulses. As such, when the extraction voltage pulses are applied between the substrate 258 and plasma 266, ions are extracted in pulsed form from the plasma 266, generating a plurality of ion pulses that are directed to the substrate 258.

Figure 9:
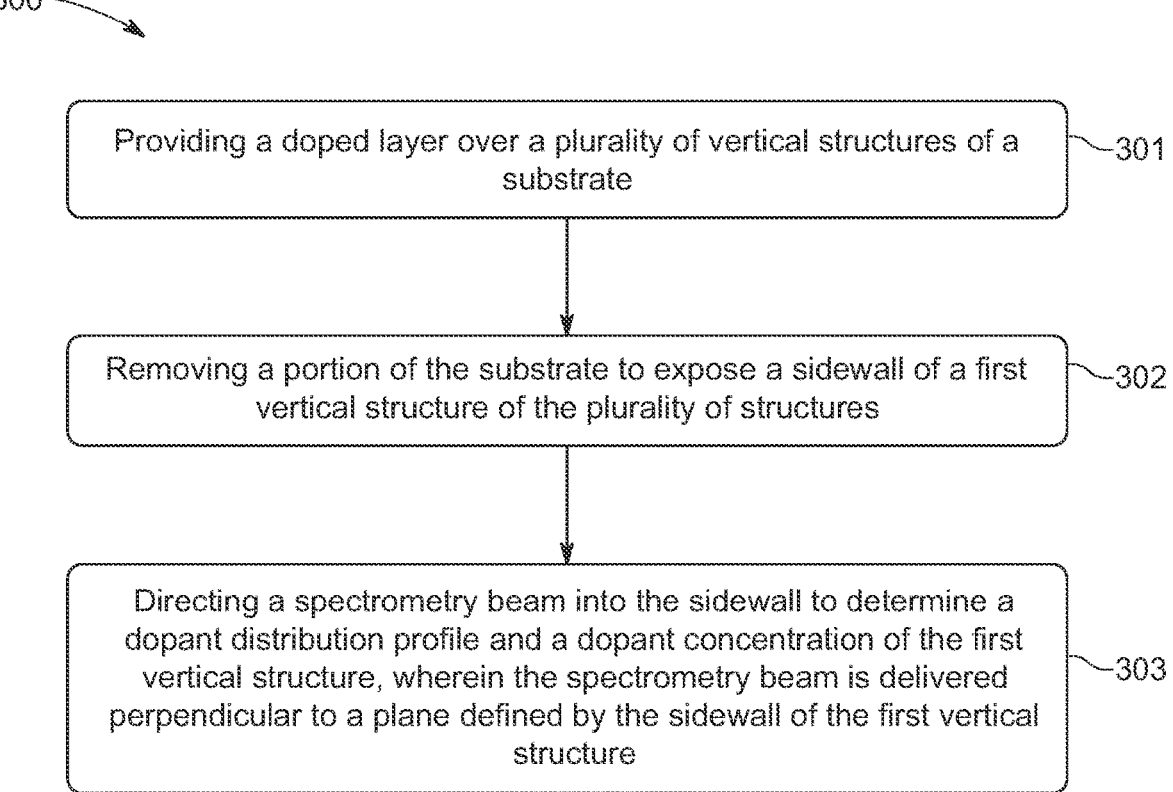
FIG. 9 is a flowchart of a method for processing the substrate and measuring dopant characteristics of the substrate, according to embodiments of the present disclosure.

Turning now to FIG. 9, a method 300 according to embodiments of the disclosure will be described. At block 301, the method 300 may include providing a doped layer over the plurality of vertical structures of a substrate. In some embodiments, the doped layer may be formed using a PLAD process.

At block 302, the method 300 may include removing a portion of the substrate to expose a sidewall of a first vertical structure of the plurality of structures. In some embodiments, the substrate is cleaved using a PMC process.

At block 303, the method 300 may include directing a spectrometry beam into the sidewall of the first vertical structure to determine a dopant distribution profile and a dopant concentration of the first vertical structure, wherein the spectrometry beam is delivered perpendicular to a plane defined by the sidewall of the first vertical structure.

In some embodiments, determining the dopant distribution profile and the dopant concentration of the first vertical structure includes performing a first measurement by directing the spectrometry beam into the plurality of vertical structures, wherein the spectrometry beam is directed parallel to the sidewall of the first vertical structure of the plurality of structures, and then performing a second measurement when the spectrometry beam is delivered perpendicular to the plane defined by the sidewall of the first vertical structure. In some embodiments, the first measurement is performed by directing a 1.5 D secondary ion mass spectrometry beam into the sidewall of the first structure. In some embodiments, directing the spectrometry beam into the sidewall of the first structure during the second measurement may include directing a secondary ion mass spectrometry beam into a plurality of locations along the sidewall of the first structure.

For the sake of convenience and clarity, terms such as "top," "bottom," "upper," "lower," "vertical," "horizontal," "lateral," and "longitudinal" will be understood as describing the relative placement and orientation of components and their constituent parts as appearing in the figures. The terminology will include the words specifically mentioned, derivatives thereof, and words of similar import.

As used herein, an element or operation recited in the singular and proceeded with the word "a" or "an" is to be understood as including plural elements or operations, until such exclusion is explicitly recited. Furthermore, references to "one embodiment" of the present disclosure are not intended as limiting. Additional embodiments may also incorporating the recited features.

Furthermore, the terms "substantial" or "substantially," as well as the terms "approximate" or "approximately," can be used interchangeably in some embodiments, and can be described using any relative measures acceptable by one of ordinary skill in the art. For example, these terms can serve as a comparison to a reference parameter, to indicate a deviation capable of providing the intended function. Although non-limiting, the deviation from the reference parameter can be, for example, in an amount of less than 1%, less than 3%, less than 5%, less than 10%, less than 15%, less than 20%, and so on.

Still furthermore, one of ordinary skill will understand when an element such as a layer, region, or substrate is referred to as being formed on, deposited on, or disposed "on," "over" or "atop" another element, the element can be directly on the other element or intervening elements may also be present. In contrast, when an element is referred to as being "directly on," "directly over" or "directly atop" another element, no intervening elements are present.

As used herein, "depositing" and/or "deposited" may include any now known or later developed techniques appropriate for the material to be deposited including yet not limited to, for example: chemical vapor deposition (CVD), low-pressure CVD (LPCVD), and plasma-enhanced CVD (PECVD). Additional techniques may include semi-atmosphere CVD (SACVD) and high density plasma CVD (HDPCVD), rapid thermal CVD (RTCVD), ultra-high vacuum CVD (UHVCVD), limited reaction processing CVD (LRPCVD), metal-organic CVD (MOCVD), and sputtering deposition. Additional techniques may include ion beam deposition, electron beam deposition, laser assisted deposition, thermal oxidation, thermal nitridation, spin-on methods, physical vapor deposition (PVD), atomic layer deposition (ALD), chemical oxidation, molecular beam epitaxy (MBE), plating, evaporation.

While certain embodiments of the disclosure have been described herein, the disclosure is not limited thereto, as the disclosure is as broad in scope as the art will allow and the specification may be read likewise. Therefore, the above description is not to be construed as limiting. Instead, the above description is merely as exemplifications of particular embodiments. Those skilled in the art will envision other modifications within the scope and spirit of the claims appended hereto.

What is claimed is:

1. A method, comprising:
providing a substrate including a plurality of alternating structures and trenches;
removing a portion of the substrate to expose a sidewall of a first structure of the plurality of structures; and
directing a spectrometry beam into the sidewall of the first structure to determine a dopant characteristic of the first structure, wherein the spectrometry beam is delivered perpendicular to a plane defined by the sidewall of the first structure.

2. The method according to claim 1, further comprising doping each of the plurality of alternating structures and trenches prior to removing the portion of the substrate.

3. The method of claim 1, wherein determining the dopant characteristic of the first structure comprises:
performing a first measurement by directing the spectrometry beam into the plurality of alternating structures and trenches, wherein the spectrometry beam is directed parallel to the sidewall of the first structure of the plurality of structures; and
performing a second measurement when the spectrometry beam is delivered perpendicular to the plane defined by the sidewall of the first structure.

4. The method according to claim 3, wherein determining the dopant characteristic of the first structure comprises determining a dopant distribution profile based on the first measurement and the second measurement.

5. The method according to claim 3, wherein determining the dopant characteristic of the first structure comprises determining a dopant concentration based on the first measurement and the second measurement.

6. The method of claim 3, wherein the first measurement is performed by directing a 1.5 D secondary ion mass spectrometry beam into the sidewall of the first structure.

7. The method of claim 1, wherein directing the spectrometry beam into the sidewall of the first structure comprises directing a secondary ion mass spectrometry beam into a plurality of locations along the sidewall of the first structure.

8. The method of claim 1, wherein removing the portion of the substrate comprises cleaving the substrate, through the first structure, using a precision micro cleaver.

9. The method of claim 8, further comprising rotating the substrate on an exterior edge after the substrate is cleaved.

10. A method for determining dopant characteristics of a plurality of vertical structures of a substrate, the method comprising:
providing a doped layer over the plurality of vertical structures;
removing a portion of the substrate to expose a sidewall of a first vertical structure of the plurality of structures; and
directing a spectrometry beam into the sidewall of the first vertical structure to determine a dopant distribution profile and a dopant concentration of the first vertical structure, wherein the spectrometry beam is delivered perpendicular to a plane defined by the sidewall of the first vertical structure.

11. The method of claim 10, wherein determining the dopant distribution profile and the dopant concentration of the first vertical structure comprises:
performing a first measurement by directing the spectrometry beam into the plurality of vertical structures, wherein the spectrometry beam is directed parallel to the sidewall of the first vertical structure of the plurality of structures; and
performing a second measurement when the spectrometry beam is delivered perpendicular to the plane defined by the sidewall of the first vertical structure.

12. The method of claim 11, wherein the first measurement is performed by directing a 1.5 D secondary ion mass spectrometry beam into the sidewall of the first vertical structure.

13. The method of claim 10, wherein directing the spectrometry beam into the sidewall of the first vertical structure comprises directing a secondary ion mass spectrometry beam into a plurality of locations along the sidewall of the first vertical structure.

14. The method of claim 10, wherein removing a portion of the substrate comprises cleaving the substrate, through the first vertical structure, using a precision micro cleaver.

15. The method of claim 14, further comprising rotating the wafer on an exterior edge after the substrate is cleaved.

* * * * *